United States Patent [19]

Boyle et al.

[11] Patent Number: 5,721,339

[45] Date of Patent: *Feb. 24, 1998

[54] GAMMA ANTIGEN OF PATHOGENIC GROUP B STREPTOCOCCI

[75] Inventors: Michael D. P. Boyle, Maumee, Ohio; L. Jeannine Brady, Gainesville, Fla.

[73] Assignee: University of Florida Research Foundation, Inc., Gainesville, Fla.

[*] Notice: The term of this patent shall not extend beyond the expiration date of Pat. No. 5,098,827.

[21] Appl. No.: 481,582

[22] Filed: Jun. 7, 1995

Related U.S. Application Data

[62] Division of Ser. No. 259,350, Jun. 14, 1994, Pat. No. 5,472,696, which is a continuation of Ser. No. 855,813, Mar. 23, 1992, abandoned, which is a continuation-in-part of Ser. No. 160,616, Feb. 26, 1988, Pat. No. 5,098,827.

[51] Int. Cl.[6] .................... A61K 39/02; A23J 3/20; C07K 16/12
[52] U.S. Cl. ............ 530/350; 530/388.4; 530/389.5; 530/820; 530/413; 424/244.1; 424/165.1
[58] Field of Search ................... 424/244.1, 165.1; 530/413, 350, 388.4, 389.5, 820

[56] References Cited

U.S. PATENT DOCUMENTS 4,789,735  12/1988  Frank et al. .
5,098,827   3/1992  Boyle et al. .

OTHER PUBLICATIONS

Sofer et al. "Current Applications of Chromatography in Biotechnology" Bio/Technology 4:712–715 1986.

Mueller, W. et al. (1989) "Qualitative or quantitative analysis for group B Streptococcus type III or its soluble type" Chemical Abstracts 110(15):391, abstract No. 131798d.

Jackson, M.K. et al. (1987) "Growth of Group B Streptococi in Amniotic Fluid of Different Gestation Ages" Abstracts of the Annual Meeting, p. 50, abstract No. B–152.

Valtonen, M.V. et al. (1986) "Isolation of a C (Ibc) protein from group B Streptococcus which elicits mouse protective antibody" Microbial Pathogenesis 1:191–204.

Kasper, D.L. et al. (1987) "Purification from type III and type I a/c group B Streptococcus respectively of antigenic disosaccarides and C surface protein useful for vaccine preparation and immunization against microorganisms" PCT Int. Appl. WO 87/06267, Chemical Abstracts 108(15):603, abstract No. 130073k.

Brady, L.J. et al. (1988) "Two Novel Antigens Associated with Group B Streptococci Identified by a Rapid Two-Stage Radioimmunoassay" The Journal of Infectious Diseases 158(5):965–972.

Oellerich, M. (1984) "Enzyme–Immunoassay: A Review" J. Clin. Chem. Clin. Biochem. 22(12):895–904.

SIGMA Chemical Company (1987) "Protein A" Biochemical and Organic Compounds for Research and Diagnostic Clinical Reagents, pp. 1142–1144.

Russell–Jones, G.J., E.C. Gotschjlich (1984) "Idenification of Protein Antigens of Group B Streptococci with Special Reference to the Ibc Antigens" J. Exp. Med. 160:1476–1484.

Russell–Jones, G.J., M.S. Blake (1984) "A Surface Receptor Specific for Human IgA on Group B Streptococci Possessing the Ibc Protein Antigen" J. Exp. Med. 160:1467–1475.

Strickland, D.M. et al. (1990) "Cost–Effectiveness of Intrapartum Screening and Treatment for Maternal Group B Streptococci Colonization" Am. J. Obstet. Gynecol. 163(1, part 1):4–8.

Baker, C.J. (1989) "Immunization to Prevent Group B Streptococca Disease: Victories and Vexations" The Journal of Infectious Diseases 161:917–921.

Boyer, K.M., S.P. Gotoff (1986) "Prevention of Early–Onset Neonatal Group B Streptococcal Disease with Selective Intrapartum Chemoprophylaxis" N. Engl. J. Med. 314(26):1665–1669.

Lim, D.V. et al. (1986) "Reductionof Morbidity and Mortality Rates for Neonatal Group B Streptococcal Disease through Early Diagnosis and Chemoprophylaxis" Journal of Clinical Microbiology 23(3):489–492.

Jelinkova, J. (1977) "Group B Streptococci in the Human Population" Current Topics in Microbiology and Immunology 76:127–165.

*Primary Examiner*—Anthony C. Caputa
*Attorney, Agent, or Firm*—Saliwanchik, Lloyd & Saliwanchik

[57] ABSTRACT

The subject invention concerns a novel in vitro process for identifying and quantifying native antigens on potentially pathogenic group B streptococci bacteria present in a clinical specimen. The invention process is made possible by the discovery of novel bacterial markers denoted γ and δ epitopes which are expressed by a variety of group B streptococcal strains.

4 Claims, 4 Drawing Sheets

FIG. 3

GAMMA ANTIGEN OF PATHOGENIC GROUP B STREPTOCOCCI

CROSS-REFERENCE TO A RELATED APPLICATION

The is a divisional of application Ser. No. 08/259,350, filed Jun. 14, 1994, now U.S. Pat. No. 5,472,696, which is a continuation of application Ser. No. 07/855,813, filed Mar. 23, 1992, now abandoned, which is a continuation-in-part of application Ser. No. 07/160,616, filed Feb. 26, 1988, now U.S. Pat. No. 5,098,827.

This invention was made with government support under NSF Grant No. DCB 8500512. The government has certain rights in this invention.

BACKGROUND OF THE INVENTION

Group B streptococci (GBS) are being increasingly recognized as important human pathogens. In addition to causing meningitis, bacteria, endocarditis, bronchopneumonia, arthritis, peritonitis, wound infections, abscesses, and urinary tract infections in adults, as many as 80% of group B infections occur in neonates (Jelinkova, J. [1977] Current Topics in Microbiology and Immunology 76:127–165). Approximately 30% of pregnant women have been reported to be colonized by GBS. Despite this high carriage rate, neonatal infection occurs with an incidence of only 0.5% (Lira, D. V., Morales, W. J., Walsh, A. F., and Kazanis, D. [1986] J. Clin. Micro. 23:489–492). Predisposing factors to development of disease are premature birth, prolonged rupture of membranes, overt maternal infection, and deficiency of type specific antibody (Boyer, K. M. and Gotoff, S. P. [1986] New England J. Med. 314:1665–1669). To date no one has identified a bacterial marker which would predict which streptococcal strains are more likely to cause infection.

The ability to subtype group B streptococci more comprehensively may be of value in predicting which organisms could cause sepsis, in particular neonatal sepsis. Recently, a receptor for the Fc region of human IgA was reported to be expressed on the surfaces of some strains of GBS (Russell-Jones, G. J., Gotschlich, E. C., and Blake, M.S. [1984] J. Exp. Med. 160:1467–1475). Western blot analysis of proteins extracted from these strains by treatment with detergent indicated that it may in fact be the γ antigen component of the c protein marker complex which has the ability to bind to IgA (Russell-Jones, G. J. and Gotschlich, E. G. [1984] J. Exp. Med. 160:1476–1484). Since IgA is the primary line of defense at mucosal surfaces, such as the vaginal epithelium, the ability of bacteria to bind this class of immunoglobulin molecules in a non-immune fashion might interfere with effective clearance of these microorganisms.

GBS are typed based on the presence of type specific carbohydrate antigens expressed on their surfaces, i.e., Ia, Ib, II, III, IV, and V. In addition, a protein marker called the c protein has been used as a typing marker. Subsets of serotype Ia and II and virtually all serotype Ib have been reported to express components of the c protein. The c protein had been reported to consist of two acid extractable antigens called α and β. A further level of sub-typing of group *B streptococci*, with respect to the c protein marker complex, would be desirable to identify potential pathogens.

In addition to the need to identify and sub-type GBS, there is also an urgent need to identify means of preventing GBS infections. GBS infections now account for over 40% of all neonatal sepsis in the United States resulting in over 12,000 cases and 2,500 infant deaths annually (Strickland, D. M., E. R. Yeomans, G. D. V. Hankins [1990] Am. J. Obstet. Gynecol. 163:4–8). In addition, pregnancy related morbidity occurs in nearly 50,000 women annually (Baker, C. J. [1989] J. I. D. 161:917–921). The National Academy of Sciences estimated that the cost of GBS early onset sepsis and obstetric disease exceeded $ 500 million in 1985 and listed GBS as the fourth most important cause of preventable infectious mortality in the United States (Strickland et at., supra). As discussed above, as many as 30% of pregnant women have been reported to be colonized with GBS. Despite this high degree of colonization, only a small percentage of women actually give birth to septic infants. However, those infants who do become infected have a very high rate of morbidity (particularly permanent neurologic damage) and mortality. No GBS vaccine is currently available. Early onset sepsis occurs within hours to days of birth, is associated with vertical transmission from the mother, and is associated with a mortality rate as high as 50–60%. The causative GBS are not clearly delineated within a given serotype. Until recently, no bacterial determinants have been identified which are predictive of early onset sepsis. Late onset GBS sepsis occurs days to weeks after birth, is not necessarily associated with vertical transmission, and is associated primarily with strains expressing the type III carbohydrate. Serotype III GBS are often associated with meningitis. The mortality rate from late onset sepsis is approximately 20%, but neurologic sequelae occur in approximately 50% of patients with meningitis.

Therefore, there is a great need to identify compositions and methods to reduce the susceptibility to GBS infection.

BRIEF SUMMARY OF THE INVENTION

This invention concerns novel bacterial pathogenic markers which can be used to identify organisms that are potentially to neonates. More specifically, the subject invention concerns novel bacterial markers denoted gamma and delta (γ and δ) epitopes which can be used to classify further group *B streptococci*. These novel epitopes are expressed by a variety of group *B streptococcal* strains. Many of the group *B streptococcal* strains also express the known α and γ antigens within the c protein marker complex. The group *B streptococcal* strain denoted A909, which is the international typing strain available from the ATCC repository at 12301 Parklawn Drive, Rockville, Md., as ATCC 27591, can be used to express the known antigens α and β, and the novel antigens of the subject invention, β and δ.

The discovery of the novel epitopes of the invention was enabled by a rapid two-stage radioimmunoassay (RIA) which identifies type specific antigens on the surfaces of group *B streptococci*. This improved rapid technique detects native unmodified type specific antigens on bacterial surfaces objectively and economically with results obtained within three hours. The assay utilizes intact bacteria and does not require hot acid extraction. Consequently, this method detects acid stable as well as acid-labile antigens in their native unmodified form. The RIA is semi-quantitative and uses the same type specific antisera as precipitin testing. The classical precipitin test is dependent on optimal concentrations of both antigens and antibodies for precipitation to occur resulting in the potential for false negative results. In addition, hot acid extraction procedures have the potential to change the native configuration of the bacterial antigenic determinants. These problems are not encountered with the more sensitive RIA procedure.

The subject invention further relates to the use of the γ and δ antigens as immunogenic compositions to raise an immune response to GBS. Thus, these novel antigens can be used to reduce the susceptibility of a human or animal to GBS infection.

DETAILED DESCRIPTION OF THE INVENTION

Materials and Methods

Using a radioimmunoassay (RIA) technique rather than conventional precipitin testing of bacterial hot acid extracts, we have identified two novel antigens, designated $\gamma$ and $\delta$, which are also reactive with c protein typing antiserum. The $\gamma$ antigen was detected on subsets of serotype Ia, Ib, and II GBS and could be identified in hot acid extracts by immunoelectrophoresis as well as by RIA. In contrast, the $\delta$ antigen was associated almost exclusively with serotype III strains and was not detected by conventional precipitin testing.

To determine whether a correlation exists between expression of the individual c protein associated antigens and a GBS strain's associated with symptomatic infection in newborn infants, an epidemiologic study was undertaken (Chun, C. S. Y., L. J. Brady, M. D. P. Boyle, H. C. Dillon, E. M. Ayoub [1991] J. I. D. 163:786–791). Two hundred and fifty-five GBS isolates recovered from septic neonates, healthy colonized newborns, and colonized pregnant women were typed by RIA. Univariate analysis was used to evaluate the frequency of expression of the $\alpha$, $\beta$, $\gamma$, and $\delta$ antigens and stepwise logistic regression was used in the multivariate analysis to evaluate the association of combinations of these and carbohydrate serotype antigens with occurrence of disease. Both the $\alpha$ and $\gamma$ were expressed more frequently by GBS strains associated with early onset disease than late onset disease ($p<0.001$ and $p<0.003$, respectively). The association of the $\gamma$ antigen with early onset sepsis was found to be independent of serotype ($p<0.036$) suggesting a potential role as a virulence factor in early onset disease. The $\delta$ antigen was significantly associated with strains from septic neonates (early and late) as compared with those from colonized healthy infants or pregnant females ($p<0.003$) suggesting that it too may act as a potential virulence factor in neonatal GBS sepsis.

Many in vitro studies have shown that expression of the c protein may interfere with effective clearance of GBS. Also, it has been found that antibodies to c protein constituents can provide protection against GBS in animal models (Payne, N. R., Y. Kim, P. Ferrieri [1987] Infect. and Immun. 55:1243–1251; Madoff, L. C., J. L. Michel, D. L. Kasper [1991] Infect. and Immun. 59:204–210), and immunization by extracts containing c proteins have been reported to yield protective antibodies (Valtonen, M. V., D. L. Kasper, N. J. Levy [1986] Microbial Pathogen. 1:191–204). These factors, as well as the epidemiologic data described above, provide additional support for the use of our novel antigens in an immunogenic composition.

Bacterial Strains, Media and Growth Conditions

Laboratory strains of group B streptococci were used. All strains were confirmed as group B streptococci by screening with PHADEBACT STREPTOCOCCUS TEST, a slide coagglutination test for identifying Groups A, B, C, and G streptococci (Pharmacia Diagnostics, Piscataway, N.J.). Bacteria were grown as stationary cultures in Todd-Hewitt broth (Difco, Detroit, Mich.) for 18–24 hr at 37° C. The bacteria were harvested by centrifugation and washed in 0.15 M phosphate buffered saline (PBS), pH 7.2. Stock cultures were stored in glycerol at −70° C. Sodium azide was added to a final concentration of 0.02% to stored culture supernatants.

Source of Group B streptococci Typing Antiserum

Rabbit anti-type Ia, Ib, II, and III carbohydrate antigens, as well as rabbit anti-c protein antigen, were kindly provided by Dr. R. Facklam, Center for Disease Control, Atlanta, Georgia.

Adsorption of Anti-c Protein Typing Antiserum

Bacterial strains expressing the reactivities to be depleted from the anti-c antiserum were chosen as appropriate adsorbents after characterization in the two-stage RIA described below. The bacteria from 5 ml of a Todd-Hewitt broth overnight culture were pelleted by centrifugation and washed once with 2 ml of PBS, pH 7.2. A 100 µl sample of anti-c protein antiserum was added to the washed bacterial pellet and rotated at 4° C. for 1 hour. The adsorption was repeated at least twice or until all reactivity against the adsorbing strain was eliminated as detected by the two-stage RIA.

Source of Protein A

The type I bacterial Fc receptor, staphylococcal Protein A, was purchased from Pharmacia Fine Chemicals, Piscataway, N.J.

Iodination of Protein A

Protein A was radioiodinated by the mild lactoperoxidase method using Enzymobeads, a reagent used to facilitate the iodination of proteins (Bio-Rad, Richmond, Calif.) (Reis, K. J., Ayoub, E. M., and Boyle, M. D. P. [1983] J. Immunol. Meth. 59:83–94). The labeled protein was separated from free iodine by passage over a G25 column, a gel filtration matrix used for desalting (PL 10, Pharmacia) and collected in veronal buffered saline, pH 7.4 containing 0.001M $Mg^{++}$, 0.00015M $Ca^{++}$, and 0.1% gelatin (VBS gel, Reis et al., supra). Proteins labeled by this method routinely have a specific activity of approximately 0.3 mCi/mg (Reis et al. supra).

Hot Acid Extracts of Group B streptococci

Laboratory strains to be hot acid extracted were inoculated into 10 ml Todd-Hewitt broth starter culture tubes. After 6–8 hours of growth the cultures were transferred to vessels containing 150 ml of sterile Todd-Hewitt broth and grown to late log phase at 37° C. (18–24 hours). The bacteria were harvested by centrifugation and extracted following the method of Lancefield (Wilkinson, H. W., Facklam, R. R., Wortham, E. C. [1973] Infect. Immun. 8:228). Essentially, the bacterial pellet was resuspended in approximately 1 ml 0.2 N HCl in 0.85% NaCl. These suspensions were boiled for 10 minutes then adjusted to neutral pH by the addition of 0.2 N NaOH. Suspensions were centrifuged at 10,000 xg for 30 minutes to remove bacterial debris and the supernatants were decanted.

Precipitin Assay for Typing Group B streptococci

Hot acid extracts were reacted with antisera of appropriate specificity and reactivity determined by precipitation in capillary tubes or by radial immunodiffusion in agarose gel (Jensen, N. E. [1979] Acta Path. Microbiol. Stand. 87:77–83).

Immunoelectrophoresis

Hot acid extracts of GBS strains were concentrated 10-fold using a MINICON MACROSOLUTE CONCENTRATOR (Amicon, Danvers, Ma). The concentrated hot acid extracts were applied to the wells of an agarose plate (Hyland DIAGNOSTICS AGAROSE GEL IEP SYSTEM, Malvern, Pa.) which was then subjected to electrophoresis at 30 mAmps for 40 minutes. The agarose from the pre-cut troughs was removed and anti-c protein marker typing serum was applied. The plates were incubated overnight at 4° C. in a moist chamber. After being soaked in PBS, pH 7.2, for 48 hours and in deionized water for 12 hours, the plates were stained with 0.7% amido black in 7% acetic acid for 5 minutes. Destaining was done with 7% acetic acid until all background color was removed.

Radioimmunoassay for Determination of Subtypes of group B streptococcal strains

A two-stage radioimmunoassay (RIA) was employed to detect type specific antigens on the bacterial cell surface. Laboratory strains were inoculated into 10 ml Todd-Hewitt broth starter culture tubes and grown to late log phase at 37° C. (18 to 24 hours). The bacteria were pelleted by centrifugation for 8 minutes at 1,000 xg, and the bacterial pellets were resuspended in 2 ml PBS, pH 7.4. Tubes containing 100 μl of bacterial suspension were incubated for 1 hour at 37° C. with 100 μl of a 1:400 dilution of each type specific antiserum; anti-Ia, anti-Ib, anti-II, anti-III or anti-c antibody following selective adsorption. Normal rabbit serum was included in each assay as a control for specificity. Following incubation, the tubes were centrifuged for 8 minutes at 1,000 xg and the bacterial pellet washed with 2 ml PBS, pH 7.2, to remove unbound antibodies. The pellets were resuspended after the wash by vortexing, and bacterial-bound antibody was quantitated by addition of 100 μl of $^{125}$I labeled Protein A containing approximately 30,000 cpm. This Fc receptor has a high affinity for rabbit immunoglobulin and, therefore, binds to any bacterial-associated antibodies. The tubes were incubated for 1 hr at 37° C. and the bacterial pellets washed twice with 2 ml of metal-free VBS containing 0.01 M ethylenediaminetetraacetic acid (EDTA) and 0.1% gelatin (EDTA-gel) to remove any labeled tracer not associated with a bacterial antigen-antibody complex. The bacterial-associated radioactivity was quantitated in a Beckman 5500 auto-gamma counter. The background level of radioactivity was determined to control tubes containing bacteria and radiolabeled Protein A only. Since the expression of a bacterial receptor that would bind antibody molecules non-specifically would complicate our assay, we have included a normal rabbit serum control in all of our assays.

Following are examples which illustrate procedures, including the best mode, for practicing the invention. These examples should not be construed as limiting. All percentages are by weight and all solvent mixture proportions are by volume unless otherwise noted.

EXAMPLE 1

Testing of GBS Strains

Fifty-three group B streptococcal (GBS) strains were tested for the presence of type specific carbohydrate antigens and protein antigens by the two-stage radioimmunoassay (RIA) described in the Methods. These strains were also typed by the conventional precipitin test of hot acid extracts, with reactivity detected by radial immunodiffusion as described in the Methods. There was an absolute correlation between the carbohydrate antigens detected by each assay (see Table 1). Strain HG782 was particularly interesting because it demonstrated two carbohydrate antigens. This was originally believed to be a mixture of two strains. Consequently, the RIA was repeated on cultures of fifteen individual colonies from this isolate and identical results were obtained. FIGS. 1A–1D show analysis of type specific carbohydrate antigen on the surface of group B streptococci using the two-stage radioimmunoassay outlined in the Methods. The height of each line depicts the amount of $^{125}$I Fc receptor associated with each strain minus the background radioactivity, thus giving a measure of the quantity of each specific antiserum associated with the bacterial pellet. A comparison of the results obtained using this assay and the classical precipitin assays are presented in Table 1. The results presented in FIG. 1A–1D demonstrate that variation in the quantities of type specific carbohydrate antigens expressed on various strains was detected by the two-stage RIA. The results obtained by the RIA were reproducible from day to day with each strain being typed on at least two occasions with identical results. In contrast to the semi-quantitative results obtained by RIA, precipitin tests of hot acid extracts indicated only the presence of a given carbohydrate.

EXAMPLE 2

Characterizing Antigens Within the c Protein Marker Complex

When the two approaches, described in Example 1, were applied to characterizing antigens within the c protein marker complex, a much more complicated pattern emerged. Reactivity with antisera against the c protein complex was detected by RIA in 36/53 strains and by precipitin test in 20/53 strains (see Table 2). In order to analyze the reasons for these differences, the two-stage RIA was repeated with a series of anti-c protein antisera which had been selectively adsorbed with bacteria showing different c protein reactivity profiles (see FIGS. 2A–2J). FIG. 2A–2E show analysis of c protein antigens on the surface of group B streptococci using the two-stage radioimmunoassay. The antiserum used in the assays is either the unabsorbed anti-c antiserum (bottom panel) or the same antiserum that has been adsorbed with selective bacteria demonstrating unique reactivities as detailed in Table 3. The height of each line depicts the amount of $^{125}$I labeled bacterial Fc receptor associated with each strain minus the background radioactivity, thus giving a measure of the quantity of each specific antiserum associated with the bacterial pellet. FIGS. 2F–2J further analysis of unique antigens within the c protein marker complex using antisera selective for α, β, γ, and δ antigens of the c protein marker complex. These specific antisera were prepared by selective adsorption of the CDC anti-c typing serum as described in Table 3. Using this approach a variety of distinct binding patterns were observed which could be accounted for by a minimum of four separate epitopes. The bacteria were also tested with anti-c antisera which had been adsorbed with the group A strain R-28 demonstrating that none of the reactivities detected were due to the R protein antigen (see FIG. 2F–2J).

EXAMPLE 3

Expression of Antigens by Strain A909 ATCC 27591

Figure 1A:
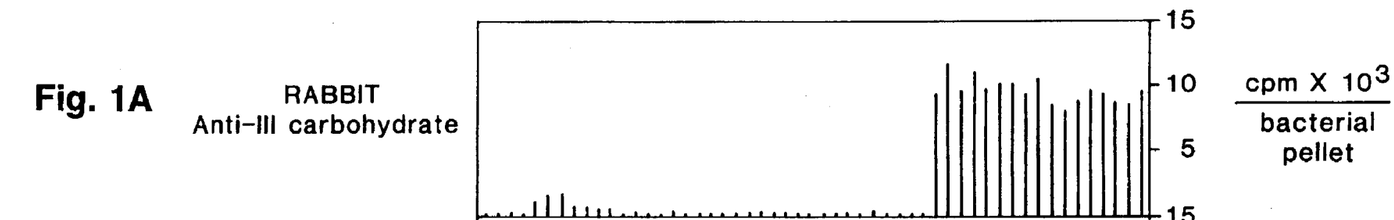
FIGS. 1A–1D shows analysis of type specific carbohydrate antigens on the surface of group B streptococci.
Figure 1B:
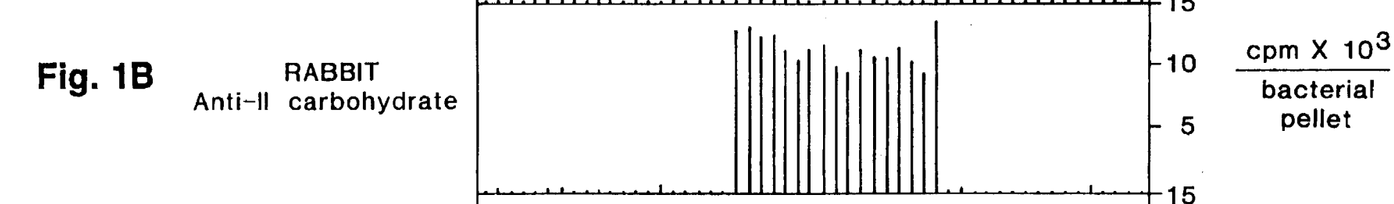
Figure 1C:
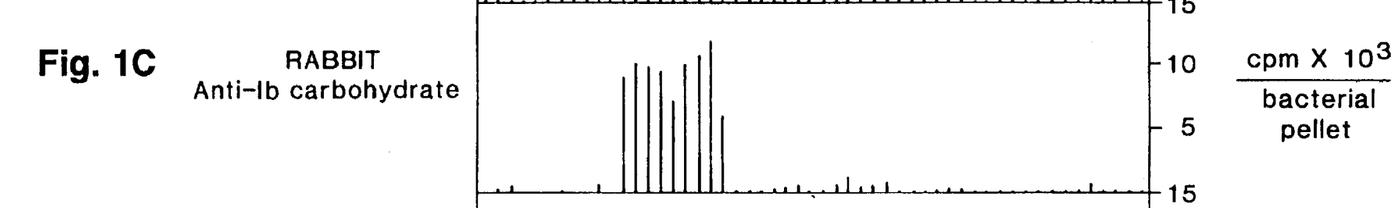
Figure 1D:
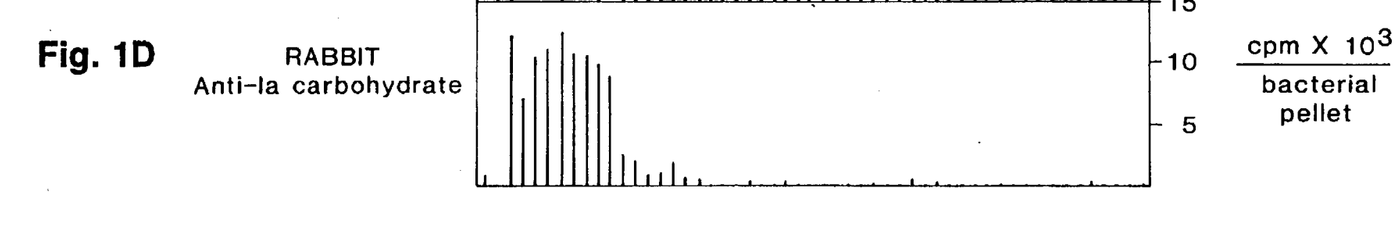
Figure 2A:
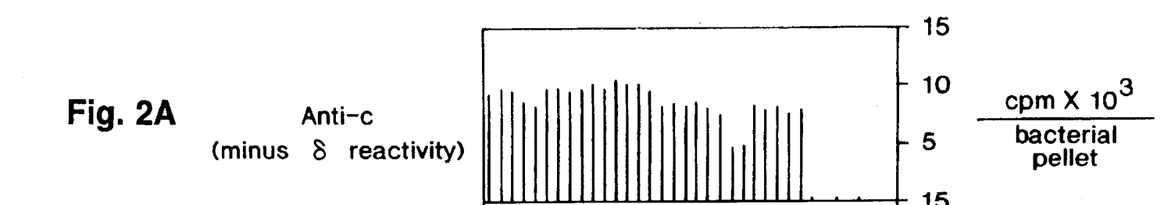
FIGS. 2A–2E shows analysis of c protein antigens on the surface of group B streptococci.
Figure 2B:
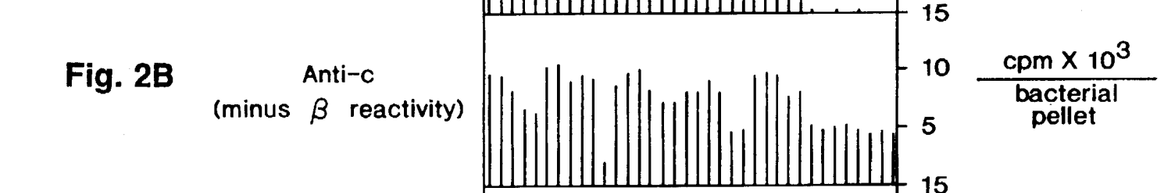
Figure 2C:
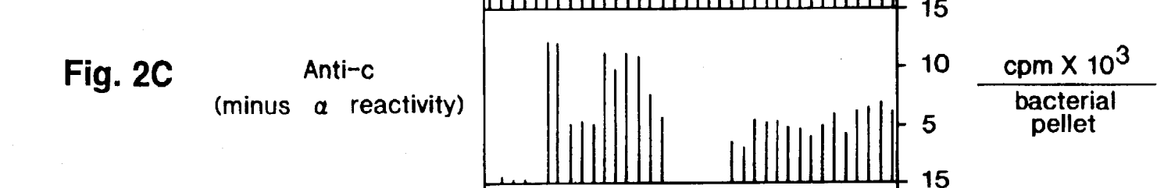
Figure 2D:
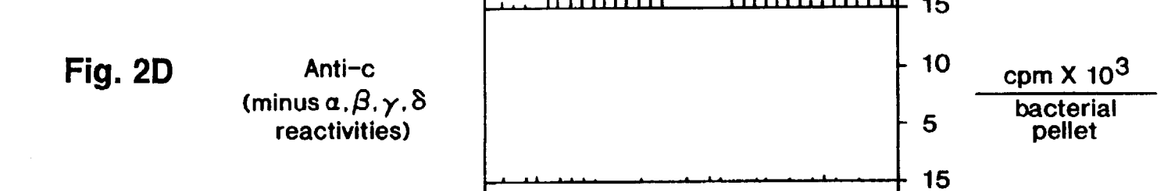
Figure 2E:
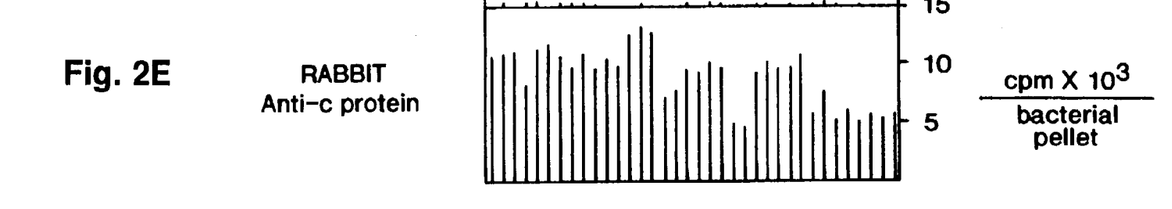
Figure 2F:
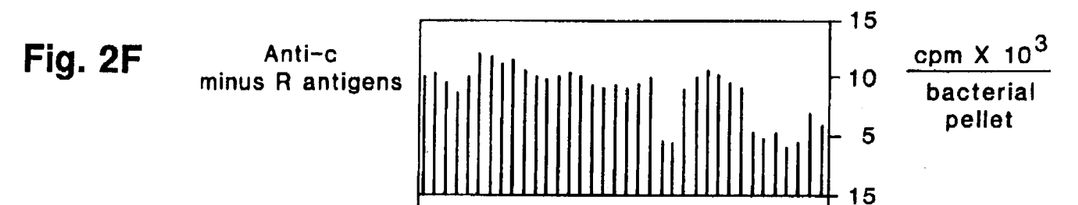
FIGS. 2F–2J shows further analysis of unique antigens within the c protein marker complex.
Figures 2G, 2H:
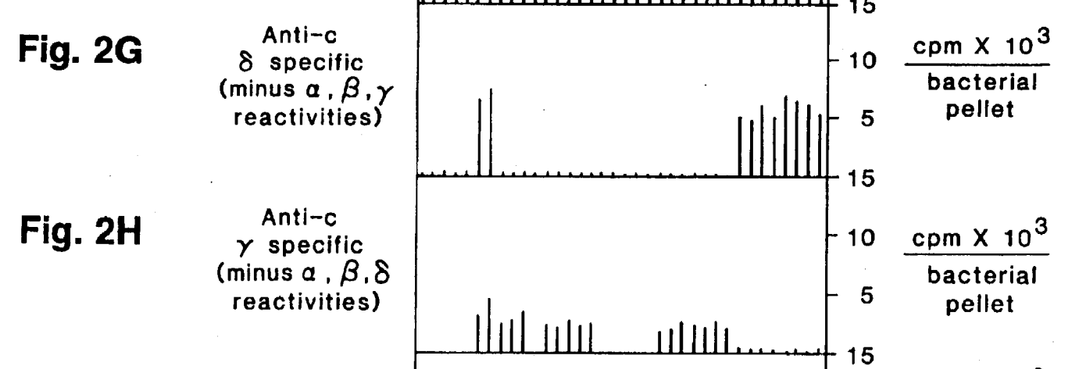
Figures 2I, 2J:
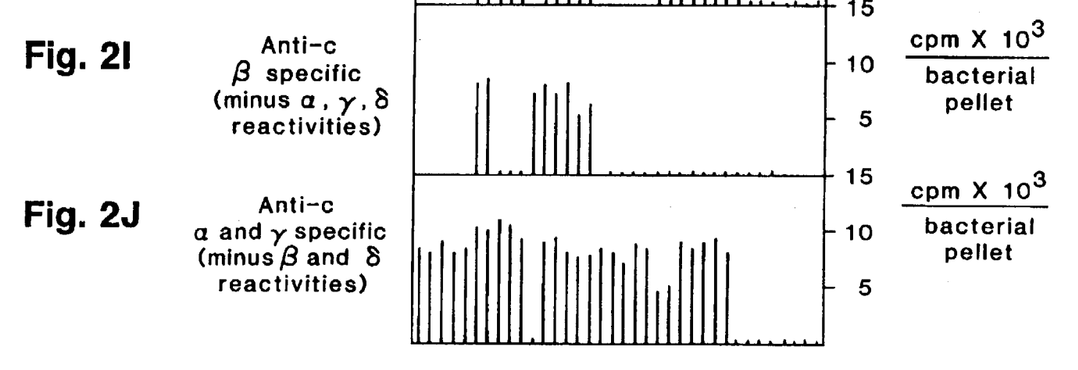
Figure 3:
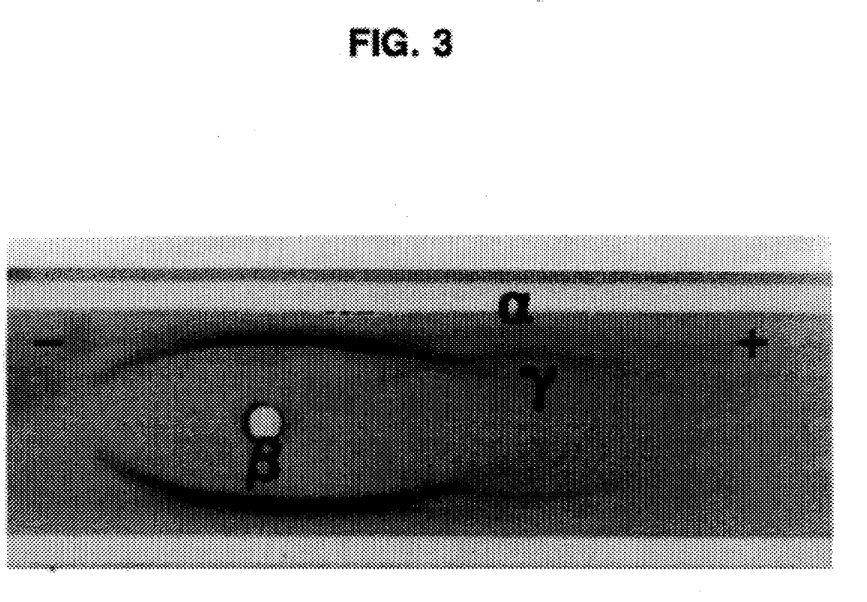
FIG. 3 shows immunoelectrophoresis of extract of prototype 1a/c strain A909.

The A909 strain expressed all four reactivities as detected by the RIA. This is the Lancefield prototype Ia/c strain which is used by CDC to prepare the c protein typing antiserum used in this study. In an attempt to identify the nature of the reactive antigens, a 10-fold concentrated hot acid extract of this strain was analyzed by immunoelectrophoresis (IEP) (see FIG. 3). FIG. 3 shows immunoelectrophoresis of a ten-fold concentrate of a hot acid extract of prototype Ia/c strain A909, developed against polyclonal rabbit anti-c protein marker typing serum. Two of the resulting precipitin arcs correspond to the previously reported α and β antigens observed by Bevanger (Bevanger, L. and Iversen, O. J. [1981] Acta Path. Microbiol. Scand. 89:205–209). In addition, a precipitation line corresponding to a third reactivity was observed (see FIG. 3). This antigen corresponded to the γ reactivity demonstrated by RIA. The γ epitope has not been detected by IEP in the past and can only be seen after concentration of the hot acid extracts. The fourth reactivity, δ, could not be detected by IEP even when hot acid extracts were concentrated 50-fold. The inability of hot acid extracts of δ-bearing strains to competitively inhibit the δ-reactivity in the two-stage RIA indicates that either δ is not acid-extractable or it is acid labile. In contrast, solubilized antigens present in hot acid extracts of α, β, and γ bearing strains were able to inhibit those corresponding reactivities in the two-stage RIA.

These results suggest that the c protein marker complex represents a more complicated antigenic structure than has been recognized previously. Furthermore, since the precipitin test is a qualitative one and is dependent on optimal concentrations of antigen and type specific antisera, low levels of one or more components of the c protein complex may lead to false negative results. However, low levels of any surface antigen would be detectable in the more sensitive RIA.

EXAMPLE 4

Preparation of Monospecific Antisera

Monospecific antisera against β, γ, and δ epitopes have been prepared by selective absorption with combinations of strains bearing all other reactivities (see Table 3). *Streptococcus agalactiae* strains PF65BV, PF549AR-B, TC795, and Perihew (PEH) were deposited with the American Type Culture Collection, 12301 Parklawn Drive, Rockville, Md. 20852 USA, on Jun. 10, 1991 and were assigned the accession numbers ATCC 55191, ATCC 55192, ATCC 55193, and ATCC 55194, respectively.

The subject cultures have been deposited under conditions that assure that access to the cultures will be available during the pendency of this patent application to one determined by the Commissioner of Patents and Trademarks to be entitled thereto under 37 CFR 1.14 and 35 U.S.C. 122. The deposits are available as required by foreign patent laws in countries wherein counterparts of the subject application, or its progeny, are filed. However, it should be understood that the availability of the deposits does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of a deposit, and in any case, for a period of at least thirty (30) years after the date of deposit or for the enforceable life of any patent which may issue disclosing the cultures. The depositor acknowledges the duty to replace the deposits should the depository be unable to furnish a sample when requested, due to the condition of a deposit. All restrictions on the availability to the public of the subject culture deposits will be irrevocably removed upon the granting of a patent disclosing them.

Specific antisera against α could not be generated since we were unable to find a strain that expressed γ that did not also express α. Strains expressing α alone could be identified by comparison of results using γ specific, versus α plus γ specific, antisera. Each of the 53 strains was characterized based on its reactivity with each of the individual carbohydrate typing antisera, as well as the polyclonal unabsorbed, and monospecific absorbed, anti-c protein complex typing sara (see Tables 1 and 2).

EXAMPLE 5

Summary of Incidence of Antigens

Table 4 summarizes the incidence of each antigen detected by the two-stage RIA. There were 2/53 strains found to have no type specific carbohydrate. Type Ia and Ib antigens were each detected on 9/53 strains and type II and III antigen were each seen on 16/53 strains. As mentioned, one strain bears both type II and III antigens. At least one component of the c protein marker complex was seen on 68% or 36/53 of the group B streptococcal strains tested by RIA. The α antigen was the most widely detected epitope and was present on 27/53 strains. A subset of strains bearing the α antigen expressed the γ reactivity. Seventeen of the 27 α-positive strains expressed the γ epitope which was never detected on a strain that did not also have the α antigen. The δ reactivity was detected on 10 strains. With the exception of the two strains which bear all four RIA reactivities (both type Ia/c), this epitope was detected only on type III strains and was the only c protein component associated with these strains. The β antigen was the least common c protein reactivity found on GBS and was detected on the surfaces of 8/53 strains screened.

EXAMPLE 6

Testing a Clinical Specimen

A clinical specimen, for example, body fluids, swabs of tissue and tissue itself, and the like can be tested, for example, in accord with the following procedures:

1. Vaginal cultures can be obtained using CULTURETTE II dual swabs, a dual swab transport device for anaerobic or aerobic bacteria that contains modified Stuarts' transport media, (Marion Scientific Corp., Kansas City, Mo.);
2. Inoculate each swab into 2 ml of LIM GROUP B STREP BROTH, a media used for the selective enrichment of Group *B streptococci*, (Gibco Laboratories, Madison, Wis.) and incubate for at least 6 hours at 37° C.;
3. Test broth cultures for GBS by slide coagglutination using PHADEBACT STREP B test for identifying group B, Pharmacia Diagnostics, Piscataway, N.J.);
4. Isolate GBS by streaking onto Blood Agar Plates (Difco);
5. Inoculate isolated GBS colonies into 10 ml Todd-Hewitt broth tubes and incubate for 6 to 24 hours at 37° C.; and
6. Conduct two stage RIA as described in the Materials and Methods section, supra.

Other examples of clinical specimens are cerebral spinal fluid, amniotic fluid, cervical swabs, blood, lung lavage, urethral swabs, rectal swabs, throat swabs, umbilical swabs, saliva, and the like.

The subject invention can be used to identify and quantify native antigens on potentially pathogenic group B streptococci bacteria present in clinical specimens of mammals, for example, humans and cows. Particularly important are pregnant mammals.

In addition to the previously-described uses, the subject invention also is useful for epidemiological studies. For example, the invention can be used to trace zoonotic sources of group B streptococcal outbreaks. Further, the invention can be used to trace nosocomial sources of group B streptococcal outbreaks in hospitals, in particular, newborn nurseries. Further, there may be as yet undiscovered biological properties of the novel γ and δ antigens described herein, analogous to the ability of the β antigen to bind IgA, which would impact on their capacity to cause disease. In addition, the association of these antigens with the pathogenicity of GBS makes these antigens particularly advantageous for use in immunogenic compositions such as vaccines. Such immunogenic compositions are described in greater detail below.

The novel antisera of the subject invention can be employed in a variety of immunotechnology procedures. The antisera can be immobilized and tagged with an appropriate label, such as a radioisotope, an optical label, e.g., a fluorescent tag, an enzyme, an electron dense ligand, and the like. The label may be detected by a gamma counter if the label is a radioactive gamma emitter, or by a fluorimeter, if the label is a fluorescent material. In the case of an enzyme, label detection may be done colorimetrically employing a substrate for the enzyme. All of these procedures are well known in the art. See "Applications of Bacterial Fc Receptors in Immunotechnology," Boyle, Michael D. P., BioTechniques Nov./Dec. 1984, pp. 334–339. This publication and the publications recited therein are incorporated herein by reference thereto.

Immobilization supports or substrates which can be used in the subject invention processes are any inert material generally used in immunochemical assays. Examples of such materials are beads formed of glass, polystyrene, polypropylene, dextran or other material. Other suitable solid phases include tubes or plates formed from or coated with these materials. Commercially available supports are agarose beads, IMMUNOBEADS (a solid phase affinity support reagent available in an activated form for the immobilization of proteins to the support) and AFFI-GEL 15 (a solid phase affinity support reagent for the immobilization of ligands that possess a primary amino group) activated beads. These are all trademarks of Bio-Rad, Richmond, Calif.

The antisera of the invention can be utilized in any immunoassay method which involves the ability of an antibody to recognize or react with an antigen or antigenic determinant (epitope) and the detection or assay of the resulting antigen-antibody complex.

As disclosed previously, the components to be assayed may be coupled or bonded to any assayable ligand such as a radioisotope, fluorescent tag, bio-assayable enzyme, electron dense tag, and the like. Those skilled in the art, having been exposed to the principles of the present invention, will be cognizant of the types of assayable ligands and methods for coupling them to the components of the methods of the present invention without the exercise of undue experimentation or inventive faculties.

For convenience and standardization, reagents for the performance of the assay can be assembled in assay kits. Two types of kits can be used.

One kit would provide for the rapid detection of unique antigens in which immobilized antiserum to native components within the c protein marker complex, for example, α, β, γ, and δ, are mixed with group B streptococcal bacteria and agglutination is measured. A positive agglutination reaction indicates the presence of the corresponding antigen to the immobilized antibody. Thus, this type of kit would contain (a) immobilized antiserum; α, β, γ, δ;

(b) a culture of intact group B streptococcal bacteria;

(c) a negative control using immobilized normal serum; and (d) a positive control using bacteria known to express the desired antigen Another type of kit uses immobilized antigens from the c protein marker complex to quantify levels of specific antibodies. This testing can be used to identify individuals having a potential risk for infection by group B streptococcal bacteria carrying the particular antigen. This type of kit would contain (a) immobilized antigen;

(b) Fc reporter, e.g., a radioisotope, an optical label, an enzyme, an electron dense ligand, and the like;

(c) normal serum control (no antibodies to any c protein marker); and (d) positive control containing specific antibody to the corresponding immobilized antigen.

If the label is an enzyme, an additional element of the kit can be the substrate for the enzyme.

Examples of enzymes which can be used as a label are lactoperoxidase, horse-radish peroxidase, alkaline phosphatase, glucose oxidase or β-glucuronidase.

Examples of radioisotope labels which can be used are $^{125}I$, $^{131}I$, $^{3}H$, $^{14}C$ or $^{35}S$.

Examples of electron dense ligand labels which can be used are ferritin, gold or horse-radish peroxidase.

EXAMPLE 7

Vaccines

The novel γ and δ antigens described herein can be used advantageously in an immunogenic composition such as a vaccine. Such a composition, when administered to a person or animal, raises antibodies or other immune response which reduces the susceptibility of that human or animal to GBS infection.

Vaccines comprising one or both of the GBS antigens, disclosed herein, and variants thereof having antigenic properties, can be prepared by procedures well known in the art. For example, such vaccines can be prepared as injectables, e.g., liquid solutions or suspensions. Solid forms for solution in, or suspension in, a liquid prior to injection also can be prepared. Optionally, the preparation also can be emulsified. The active antigenic ingredient or ingredients can be mixed with excipients which are pharmaceutically acceptable and compatible with the active ingredient. Examples of suitable excipients are water, saline, dextrose, glycerol, ethanol, or the like, and combinations thereof. In addition, if desired, the vaccine can contain minor amounts of auxiliary substances such as wetting or emulsifying agents, pH buffering agents, or adjuvants such as aluminum hydroxide or muramyl dipeptide or variations thereof. Also, cholera toxin subunit B or other agents which stimulate antibody production at mucosal sites can be used. In the case of peptides, coupling to larger molecules such as KLH or tetanus toxoid sometimes enhances immunogenicity. The vaccines are conventionally administered parenterally, by injection, for example, either subcutaneously or intramuscularly. Additional formulations which are suitable for other modes of administration include suppositories and, in some cases, oral formulations. For suppositories, traditional binders and carriers include, for example, polyalkalene glycols or triglycerides. Suppositories can be formed from mixtures containing the active ingredient in the range of about 0.5% to about 10%, preferably about 1 to about 2%. Oral formulations can include such normally employed excipients as, for example, pharmaceutical grades of mannitol, lactose, starch, magnesium stearate, sodium saccharine, cellulose, magnesium carbonate, and the like. These compositions can take the form of solutions, suspensions, tablets, pills, capsules, sustained release formulations or powders and contain from about 10% to about 95% of active ingredient, preferably from about 25% to about 70%.

The compounds can be formulated into the vaccine as neutral or salt forms. Pharmaceutically acceptable salts include the acid addition salts (formed with the free amino groups of the peptide) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The vaccines are administered in a manner compatible with the dosage formulation, and in such amount as will be therapeutically effective and immunogenic. The quantity to be administered can depend on the subject to be treated and the degree of protection desired. Advantageously, methods known to promote mucosal immunity can be combined with systemic immunity promoters to maximize protection against GBS. Also, the γ and δ antigens of the subject invention may be combined with carbohydrate antigenic components to enhance the immunogenic response and provide a broader range of protection. The combination of these antigens may be, for example, through chemical coupling. Precise amounts of active ingredient required to be administered depend on the judgment of the practitioner and can be peculiar to each individual. However, suitable dosage ranges are of the order of about several hundred micrograms active ingredient per individual. Suitable regimes for initial administration and booster shots are also variable, but are typified by an initial administration followed in one or two week intervals by a subsequent injection or other administration.

Advantageously, the vaccines of the subject invention can be formulated and administered in a manner designed specifically to induce mucosal immunity.

It should be understood that the examples and embodiments described herein are for illustrative purposes only and that various modifications or changes in light thereof will be suggested to persons skilled in the art and are to be included within the spirit and purview of this application and the scope of the appended claims.

TABLE 1

Summary of Precipitin Assay and Two Stage Radioimmunoassay to Type Group B Streptococci for Carbohydrate Antigens

| Strain | Detected by Precipitin Test | Detected by RIA | Strain | Detected by Precipitin Test | Detected by RIA |
|---|---|---|---|---|---|
| N86K | No type | No type | PF610AR | II | II |
| NP1AR | No type | No type | NPF1AV | II | II |
| HG824 | Ia | Ia | HG818 | II | II |
| SS617 | Ia | Ia | HG819 | II | II |
| HG346 | Ia | Ia | 9B200 | II | II |
| PF534AR | Ia | Ia | HG768 | II | II |
| J46 | Ia | Ia | HG804 | II | II |
| HG783 | Ia | Ia | HG774 | II | II |
| HG784 | Ia | Ia | HG782 | II | II, III |
| HG381 | Ia | Ia | HG820 | III | III |
| A909 | Ia | Ia | VC75 | III | III |
| HG812 | Ib | Ib | HG780 | III | III |
| HG806 | Ib | Ib | HG757 | III | III |
| 2AR | Ib | Ib | HG814 | III | III |
| TC795 | Ib | Ib | HG754 | III | III |
| PF549AR-B | Ib | Ib | HG802 | III | III |
| HG805 | Ib | Ib | HG738 | III | III |
| HG769 | Ib | Ib | J48 | III | III |
| TC137 | Ib | Ib | J52 | III | III |
| SS618 | Ib | Ib | PEH | III | III |
| HG811 | II | II | J51 | III | III |
| PF58AV | II | II | HG786 | III | III |
| PF536AR | II | II | HG828 | III | III |
| PF549AR-NB | II | II | HG770 | III | III |
| PF541AR | II | II | HG771 | III | III |
| J44 | II | II | | | |
| PF65BV | II | II | | | |

TABLE 2

Distribution of α, β, γ, and δ Antigens on Strains Reactive with Anti-c Typing Antisera Detected by RIA

| Strain | Carbohydrate Subtype | c Protein Reactivity Detected by Precipitin Test | c Protein Marker Antigens Detected by RIA | Strain | Carbohydrate Subtype | c Protein Reactivity Detected by Precipitin Test | c Protein Marker Antigens Detected by RIA |
|---|---|---|---|---|---|---|---|
| HG346 | Ia | + | α | PF25AR | II | + | α |
| PF534AR | Ia | + | α | PF610AR | II | + | α |
| J46 | Ia | + | α | NPF1AV | II | + | α |

TABLE 2-continued

Distribution of α, β, γ, and δ Antigens on Strains Reactive with Anti-c Typing Antisera Detected by RIA

| Strain | Carbohydrate Subtype | c Protein Reactivity Detected by Precipitin Test | c Protein Marker Antigens Detected by RIA | Strain | Carbohydrate Subtype | c Protein Reactivity Detected by Precipitin Test | c Protein Marker Antigens Detected by RIA |
|---|---|---|---|---|---|---|---|
| HG783 | Ia | — | α | HG818 | II | — | α, γ |
| HG784 | Ia | — | α | HG819 | II | — | α, γ |
| HG381 | Ia | + | α, β, γ, δ | 9B200 | II | + | α, γ |
| A909 | Ia | + | α, β, γ, δ | HG768 | II | — | α, γ |
| HG812 | Ib | + | α, γ | HG804 | II | — | α, γ |
| HG806 | Ib | + | α, γ | HG774 | II | — | α, γ |
| 2AR | Ib | + | α, γ | HG782 | II, III | — | α, γ |
| TF795 | Ib | + | β | J48 | III | — | δ |
| PF549AR-B | Ib | + | α, β, γ | J52 | III | — | δ |
| HG805 | Ib | + | α, β, γ | JB3 | III | — | δ |
| HG769 | Ib | + | α, β, γ | J51 | III | — | δ |
| TC137 | Ib | + | α, β, γ | HG786 | III | — | δ |
| SS618 | Ib | + | α, β, γ | HG828 | III | — | δ |
| J44 | II | + | α | HG770 | III | — | δ |
| PF65BV | II | + | α | HG771 | III | — | δ |

TABLE 3

Depletion of Component Reactivities from Anti-Ibc Typing Antiserum

| Strain(s) Used For Adsorption | Reactivities Depleted | Reactivities Remaining |
|---|---|---|
| R-28 (Group A) | R | α, β, γ, δ |
| PF65BV | α | β, γ, δ |
| TC795 | β | α, γ, δ |
| J48 | δ | α, β, γ |
| TC795, PEH | β, δ | α, γ |
| 9B200, PEH | α, γ, δ | β |
| PF65BV, TC795, J48 | α, β, δ | γ |
| PF549AR-B | α, β, γ | δ |
| HG381 | α, β, γ, δ | NONE |

TABLE 4

Summary of Typing Results (53 Strains)

| Carbohydrate Antigens | No. | % of All Strains | % of Ic Strains |
|---|---|---|---|
| No Type | 2 | 3.8 | |
| Ia | 9 | 16.0 | |
| Ib | 9 | 17.0 | |
| II | 16 | 30.2 | |
| III | 16 | 30.2 | |
| II/III | 1 | 1.9 | |
| Ic protein marker | 36 | 67.9 | 100.0 |
| α | 27 | 50.9 | 75.0 |
| β | 8 | 15.1 | 22.2 |
| γ | 17 | 32.1 | 47.2 |
| δ | 10 | 18.9 | 27.8 |

We claim:

1. A composition consisting essentially of γ antigen, wherein said γ antigen is obtained by a process comprising the steps of:

(a) raising antibodies by immunizing a host animal with an immunogenic amount of the group B Streptococci strain A909 known to express said γ antigen and having all the identifying characteristics of ATCC 27591;

(b) isolating antisera from said host that contains said antibodies;

(c) contacting said antisera with strains of group B Streptococci that express α, β, and δ antigens but that do not express said δ antigen, whereby antibodies reactive with said α, β, and δ antigens are depleted from said antisera;

(d) attaching the antisera from step (c) to a matrix material to form an immunoadsorbent matrix;

(e) contacting said immunoadsorbent matrix with an extract of cell surface antigens from group B Streptococci known to express said γ antigen, so that said γ antigen is bound to said immunoadsorbent matrix; and (f) recovering bound γ antigen from said immunoadsorbent matrix.

2. A purified antibody to the γ antigen.

3. An antibody composition consisting essentially of antibodies to the γ antigen wherein said composition is raised by immunizing a host animal with the γ antigen composition of claim 1.

4. A composition comprising antibodies to the γ antigen and no antibodies to the α antigen.

* * * * *

UNITED STATES PATENT AND TRADEMARK OFFICE
CERTIFICATE OF CORRECTION

PATENT NO. : 5,721,339

DATED : February 24, 1998

INVENTOR(S) : Michael D. P. Boyle and L. Jeannine Brady

It is certified that error appears in the above-indentified patent and that said Letters Patent is hereby corrected as shown below:

Column 1, line 19: "bacteria" should read --bacteremia--;

line 27: "(Lira," should read --(Lim,--;

line 46: "Gotschlich, E.G." should read --Gotschlich, E.C.--.

Column 2, line 8: "et at.," should read --et al.,--;

lines 33-35: "This invention concerns novel bacterial pathogenic markers which can be used to identify organisms that are potentially to neonates" should read --This invention concerns novel bacterial markers which can be used to identify organisms that are potentially pathogenic to neonates--.;

line 40: "$\alpha$ and $\gamma$ antigens" should read --$\alpha$ and $\beta$ antigens--; and     line 47: "$\beta$ and $\delta$." should read --$\gamma$ and $\delta$.--.

Column 4, line 37: "Enzymobeads" should read --ENZYMOBEADS--.

Column 5, line 2: "Stand." should read --Scand.--; and line 10: "(Hyland" should read --(HYLAND--.

UNITED STATES PATENT AND TRADEMARK OFFICE
CERTIFICATE OF CORRECTION

PATENT NO. : 5,721,339

DATED : February 24, 1998

INVENTOR(S) : Michael D. P. Boyle and L. Jeannine Brady

It is certified that error appears in the above-indentified patent and that said Letters Patent is hereby corrected as shown below:

Column 6, line 50: "FIGS. 2F-2J further analysis" should read

--FIGS. 2F-2J show further analysis--.

Column 7, line 11: "Iverson, O.J." should read --Iverson, O.-J.--.

Column 8, line 15: "sara" should read --sera--.

Column 14, line 37: "said δ antigen," should read --said γ antigen,--.

Signed and Sealed this

Eleventh Day of August 1998

*Attest:*

BRUCE LEHMAN

*Attesting Officer*  *Commissioner of Patents and Trademarks*